(12) United States Patent
Muller et al.

(10) Patent No.: US 12,023,504 B2
(45) Date of Patent: *Jul. 2, 2024

(54) METHOD AND DEVICE FOR MANAGING PACING THERAPY BASED ON INTER VENTRICULAR SEPTAL ACTIVITY

(71) Applicant: Pacesetter, Inc., Sylmar, CA (US)

(72) Inventors: David Muller, Sylmar, CA (US); Raffaele Corbisiero, Sylmar, CA (US)

(73) Assignee: Pacesetter, Inc., Sylmar, CA (US)

( * ) Notice: Subject to any disclaimer, the term of this patent is extended or adjusted under 35 U.S.C. 154(b) by 113 days.

This patent is subject to a terminal disclaimer.

(21) Appl. No.: 17/851,236

(22) Filed: Jun. 28, 2022

(65) Prior Publication Data

US 2022/0323770 A1 Oct. 13, 2022

Related U.S. Application Data

(63) Continuation of application No. 16/835,621, filed on Mar. 31, 2020, now Pat. No. 11,400,297.

(60) Provisional application No. 62/831,030, filed on Apr. 8, 2019.

(51) Int. Cl.
*A61N 1/36* (2006.01)
*A61N 1/368* (2006.01)
*A61N 1/375* (2006.01)

(52) U.S. Cl.
CPC ....... *A61N 1/36843* (2017.08); *A61N 1/3686* (2013.01); *A61N 1/3756* (2013.01)

(58) Field of Classification Search
CPC .............. A61N 1/36843; A61N 1/3686; A61N 1/3756; A61N 1/36842
See application file for complete search history.

(56) References Cited

U.S. PATENT DOCUMENTS 11,400,297 B2 * 8/2022 Muller ............... A61N 1/36842

* cited by examiner

*Primary Examiner* — Rex R Holmes
(74) *Attorney, Agent, or Firm* — Dean D. Small; The Small Patent Law Group, LLC

(57) ABSTRACT

Methods, devices and program products are provided for managing a pacing therapy using an implantable medical device (IMD). The methods, devices and program products sense cardiac activity (CA) signals at electrodes located proximate to multiple left ventricular (LV) sites and a right ventricular (RV) site of the heart and utilizing one or more processors to measure activation times between the multiple LV sites and the RV site based on the CA signals. The processors program an order of activation for the multiple LV sites based on the activation times and identify an RV activation time and a septum activation time based on the CA signals. The processors calculate a septum to RV activation time (SRAT) based on the RV and septum activation times and program an $AV_{SRAT}$ delay based on the SRAT.

20 Claims, 7 Drawing Sheets

METHOD AND DEVICE FOR MANAGING PACING THERAPY BASED ON INTER VENTRICULAR SEPTAL ACTIVITY

RELATED APPLICATION

The present application is a continuation application of, and claims priority to, U.S. application Ser. No. 16/835,621, Titled "METHOD AND DEVICE FOR MANAGING PACING THERAPY BASED ON INTERVENTRICULAR SEPTAL ACTIVITY" filed 31 Mar. 2020 (now U.S. Pat. No. 11,400,297, issued 2 Aug. 2022), which claims priority to United States Provisional Application No. 62/831,030, Titled "METHOD AND DEVICE FOR MANAGING PACING THERAPY BASED ON INTERVENTRICULAR SEPTAL ACTIVITY" which was filed on 8 Apr. 2019 (now expired), the complete subject matter of each are expressly incorporated herein by reference in their entirety.

BACKGROUND

Embodiments of the present disclosure generally relate to methods and devices for managing fusion pacing therapy for multisite left ventricular pacing based on interventricular septal activity.

Cardiac resynchronization therapy (CRT) is a process where the Left Ventricle (LV) is stimulated in conjunction with the right ventricle (RV) to provide a more synchronous and efficient contraction and has become a well-established clinical therapy for patients with symptomatic left ventricular systolic dysfunction and electrocardiographic QRS duration ≥120 milliseconds (ms). However, it has been demonstrated that CRT "non-responder" rates may approach undesirably percentages after several months. Subsequent studies utilizing echocardiographic-guided device reprogramming for provision of optimal atrio-ventricular (A-V) and interventricular (VV) delays at rest have demonstrated improved clinical response.

Recent data has demonstrated that multiple LV sites of stimulation, in addition to the RV stimulation provides an added benefit, lowers non-responder rates and increases cardiac output, results in higher response rates, and demonstrates better overall response to CRT. A new theory to incorporate all of these aspects of CRT utilizing measurements of intrinsic and paced intracardiac electrograms could provide additive improvement. These measures can now be incorporated after implantation with the addition of a quadripolar LV lead that includes four electrodes of potential stimulation and sensing and can be selected based on the measurements described herein to choose desired programming.

Clinical studies related to cardiac pacing have shown that an optimal atrio-ventricular pacing delay (e.g., AV delay or PV delay) and/or an optimal interventricular pacing delay (e.g., VV delay) can improve cardiac performance. However, such optimal delays depend on a variety of factors that may vary over time. Thus, what is "optimal" may vary over time. An optimization of AV/PV pacing delay and/or VV pacing delay may occur at implantation and sometimes, a re-optimization may occur during a follow-up consultation. While such optimizations are beneficial, the benefits may not be long lasting due to changes in various factors related to device and/or cardiac function. Various systems and methods are provided for allowing a pacemaker or IMD to determine and/or adjust AV/PV/VV pacing delays so as to help maintain the pacing delays at optimal values. In particular, techniques were set forth for exploiting various interventricular conduction delays to determine optimal AV/PV/VV pacing delays. Techniques were also set forth for exploiting the VV delays to determine which ventricles should be paced—the left ventricle (LV), the right ventricle (RV), both ventricles, or neither.

Other techniques have been set forth for determining AV/PV delays based on inter-atrial conduction delays and interventricular conduction delays. In particular, see U.S. Pat. No. 7,248,925, to Bruhns et al., entitled "System and Method for Determining Optimal Atrioventricular Delay based on Intrinsic Conduction Delays," which is fully incorporated by reference herein.

SUMMARY

In accordance with methods and systems herein, an IMD is implanted into a patient and coupled to one or more leads placed in or proximate the right ventricle (RV) and the left ventricle (LV). For example, an LV lead may be delivered via the coronary sinus to a location proximate to the LV. The LV lead includes multiple electrodes that may be stimulated in various desired sequences, termed multi-point pacing (MPP). The IMD may define one or more sensing vectors to sense intrinsic activity in connection with events of interest (e.g., an RV sensing channel). For example, the intrinsic activity travels from the atrial-ventricular (AV) node down the intraventricular septum. The intrinsic activity continues until reaching an apex of the RV. The sensing vectors sense an intrinsic RV event/contraction. The sensing vectors may extend between an RV tip electrode of the RV lead (that is configured as an anode) and one or more LV electrodes (e.g., a distal LV electrode) that is configured as the cathode. The IMD analyzes the cardiac activity sensed by the sensing vectors to detect an onset of activation of the RV septum as the RV septum begins to depolarize and a complete depolarization of the RV (corresponding to the QRS complex in an ECG signal).

During normal conduction in the heart, excitation originates in the sinoatrial (SA) node, then propagates through both atria (internodal tracts shown as dashed lines). The atrial depolarization spreads to the atrioventricular (AV) node, passes through the bundle of HIS (not labeled), and then to the Purkinje fibers which make up the left and right bundle branches; subsequently all ventricular muscle becomes activated. The bundle of HIS divides in the interventricular septum into right and left bundle branches. The right bundle branch branches off of the bundle of HIS and travels down the interventricular septum near the endocardium. The septal excitation is generally associated with generation of the "Q" deflection in an ECG signal.

In accordance with embodiments herein, methods and systems identify one or more features of interest within the interventricular septal activity and one or more features of interest from right ventricular activation and based thereon determine a septal to RV activation time (SRAT). The SRAT represents a conduction time from an initial activation time of the interventricular septum until depolarization of the RV. In addition, the methods and systems stimulate each of the electrodes on the LV leads in isolation and measure an LV-RV activation time. For example, the LV lead may include four electrodes (e.g., LV1, LV2, LV3, LV4), each of which separately generates a pacing pulse. The methods and systems measure a time for activity from each LV simulation to reach the RV electrode, thereby identifying an LV1-RV activation time, an LV2-RV activation time, an LV3-RV activation time, and an LV4-RV activation time. The LV to RV activation times are ordered by duration, and the LV to RV combination exhibiting the longest delay is utilized to determine a first LV site for stimulation. For example, when the proximal LV electrode exhibits the longest activation time (LV1-RV), the proximal LV electrode (LV1) is designated as the first site at which an LV CRT therapy is delivered. Thereafter, an order in which the remaining LV electrodes are programmed to deliver therapy is defined based on the activation times, such that the second longest delay is defined as the second LV stimulation site, the third longest delay is designated as the third LV stimulation site, etc.

Further, in accordance with embodiments herein, the methods and systems manage the timing of the CRT therapy to ensure contribution from intrinsic activation via the septum, RV, LV1, and LV2, etc. The contribution of intrinsic activation via the septum is managed based on certain conduction times. The methods and systems collect measurements acquired in both the intrinsic state, as well as with stimulating the LV from different sites. The methods and systems ensure that the intrinsic septum has an activation time prior to the RV stimulation contribution. The contribution of the intrinsic septum activation is programmed based a desired percentage of the SRAT (e.g., SRAT*0.5). This ensures the intrinsic component, which can be utilized as is or augmented with the use of the negative AV hysteresis (SyncAV offset). Next to ensure the LV portion of CRT therapy, embodiments herein manage the wavefront propagation by programming the LV cathode with longest LV-RV conduction time to begin as the first site of stimulation, followed by the second longest, etc. (allowing for future iterations with >4 poles). Subsequent to the LV, the RV should be stimulated simultaneous occurring at the fastest allowable programmed time (ideal would be LV1-LV2-RV simultaneous).

In accordance with embodiments herein a method is provided for managing a pacing therapy using an implantable medical device (IMD). The method comprising: sensing cardiac activity (CA) signals at electrodes located proximate to multiple left ventricular (LV) sites and a right ventricular (RV) site of the heart; utilizing one or more processors to perform: measuring activation times between the multiple LV sites and the RV site based on the CA signals; programming an order of activation for the multiple LV sites based on the activation times; identifying an RV activation time and a septum activation time based on the CA signals; calculating a septum to RV activation time (SRAT) based on the RV and septum activation times; and programming an $AV_{SRAT}$ delay based on the SRAT.

Optionally, the septum activation time represents an onset of a Q-wave in a QRS complex. Optionally, the sensing the CA signals includes sensing first CA signals over first sensing channel and sensing second CA signals over a second sensing channel simultaneously. The method further comprises: analyzing the first CA signals sensed over the first sensing channel to identify the RV activation; and analyzing the second CA signals sensed over the second sensing channel to identify a time of initial septum activation as the septum activation time, the septum activation time corresponding to a point in time at which the second CA signals sensed over the second sensing channel begin to rise above a baseline/neutral voltage level.

Optionally, the $AV_{SRAT}$ delay is based on an adjustment of a prior AV delay by an amount proportional to the SRAT. Optionally, the $AV_{SRAT}$ delay is set equal to the prior AV delay minus a percentage of the SRAT. Optionally, the measuring further comprises delivering a pacing pulse at one of the LV sites and detecting a related intrinsic event at the RV site, repeating the delivering and detecting operations in connection with the multiple LV sites. Optionally, the identifying the RV activation time and the septum activation time further comprises: collecting the CA signals over first and second sensing vectors; analyzing the CA signals collected over the first sensing vector to identify the RV activation time corresponding to a feature of interest in an R-wave of a QRS complex; analyzing the CA signals collected over the second sensing vector to identify the septum activation time corresponding to a feature of interest in a Q-wave of the QRS complex. Optionally, the SRAT corresponds to a duration of the interval between the feature of interest in the R-wave and the feature of interest in the Q wave of the QRS complex.

In accordance with embodiments herein, the system is provided for managing a pacing therapy using an implantable medical device (IMD), the system comprising: electrodes configured to be located proximate to multiple left ventricular (LV) sites and a right ventricular (RV) site of the heart, the electrodes configured to sense cardiac activity (CA) signals; memory to store program instructions; and one or more processors configured to implement the program instructions to perform: measuring activation times between the multiple LV sites and the RV site based on the CA signals; programming an order of activation for the multiple LV sites based on the activation times; identifying an RV activation time and a septum activation time based on the CA signals; calculating a septum to RV activation time (SRAT) based on the RV and septum activation times; and programming an $AV_{SRAT}$ delay based on the SRAT.

Optionally, the $AV_{SRAT}$ delay is based on an adjustment of a prior AV delay by an amount proportional to the SRAT. Optionally, the $AV_{SRAT}$ delay is set equal to the prior AV delay minus a percentage of the SRAT. Optionally, the processors are configured to perform the measuring by delivering a pacing pulse at one of the LV sites and detecting a related intrinsic event at the RV site, repeating the delivering and detecting operations in connection with the multiple LV sites. Optionally, the processors are configured to perform the identifying the RV activation time and the septum activation time by: collecting the CA signals over first and second sensing vectors; analyzing the CA signals collected over the first sensing vector to identify the RV activation time corresponding to a feature of interest in an R-wave of a QRS complex; analyzing the CA signals collected over the second sensing vector to identify the septum activation time corresponding to a feature of interest in a Q-wave of the QRS complex. Optionally, the SRAT corresponds to a duration of the interval between the feature of interest in the R-wave and the feature of interest in the Q wave of the QRS complex.

In accordance with embodiments herein, a system is provided for managing a pacing therapy using an implantable medical device (IMD). The system comprises: electrodes configured to be located proximate to multiple left ventricular (LV) sites and a right ventricular (RV) site of the heart, the electrodes configured to sense cardiac activity (CA) signals; memory to store program instructions; and one or more processors configured to implement the program instructions to: measure activation times between the multiple LV sites and the RV site based on the CA signals; program an order of activation for the multiple LV sites based on the activation times; identify an RV activation time and a septum activation time based on the CA signals; calculate a septum to RV activation time (SRAT) based on the RV and septum activation times; and set an $AV_{SRAT}$ delay based on the SRAT.

Optionally, the system utilizes a septum activation time that represents an onset of a Q-wave in a QRS complex. Optionally, the system further comprises first and second sensing channels configured to sense first and second CA signals, respectively, simultaneously. The one or more processors further configured to: analyze the first CA signals sensed over the first sensing channel to identify the RV activation; and analyzing the second CA signals sensed over the second sensing channel to identify a time of initial septum activation as the septum activation time, the septum activation time corresponding to a point in time at which the second CA signals sensed over the second sensing channel begin to rise above a baseline/neutral voltage level.

Optionally, the $AV_{SRAT}$ delay is based on an adjustment of a prior AV delay by an amount proportional to the S RAT. Optionally, the $AV_{SRAT}$ delay is set equal to the prior AV delay minus a percentage of the SRAT. Optionally, the processors are configured to perform the measure operation by delivering a pacing pulse at one of the LV sites and detecting a related intrinsic event at the RV site, repeating the delivering and detecting operations in connection with the multiple LV sites. Optionally, the processors are configured to identify the RV activation time and the septum activation time by: collecting the CA signals over first and second sensing vectors; analyzing the CA signals collected over the first sensing vector to identify the RV activation time corresponding to a feature of interest in an R-wave of a QRS complex; and analyzing the CA signals collected over the second sensing vector to identify the septum activation time corresponding to a feature of interest in a Q-wave of the QRS complex.

Optionally, the SRAT corresponds to a duration of the interval between the feature of interest in the R-wave and the feature of interest in the Q wave of the QRS complex. Optionally, the system further comprises an implantable medical device that includes a housing that holds the memory and one or more processors. Optionally, the system further comprises a lead that includes the electrodes, the lead coupled to the implantable medical device. Optionally, the implantable medical device is a leadless device with the electrodes provided on the housing.

Optionally, the system further comprises an implantable medical device and an external device configured to wirelessly communicate with the implantable medical device. The implantable medical device is coupled to the electrodes and configured to collect and transmit the CA signals to the external device. The external device includes one or more processors configured to: identify the RV activation time and the septum activation time based on the CA signals; calculate the SRAT based on the RV and septum activation times; calculate the $AV_{SRAT}$ delay based on the SRAT; and wirelessly transmit the $AV_{SRAT}$ delay to the implantable medical device, the implantable medical device utilizing the $AV_{SRAT}$ delay in connection with delivering therapy.

DETAILED DESCRIPTION

Figure 1:
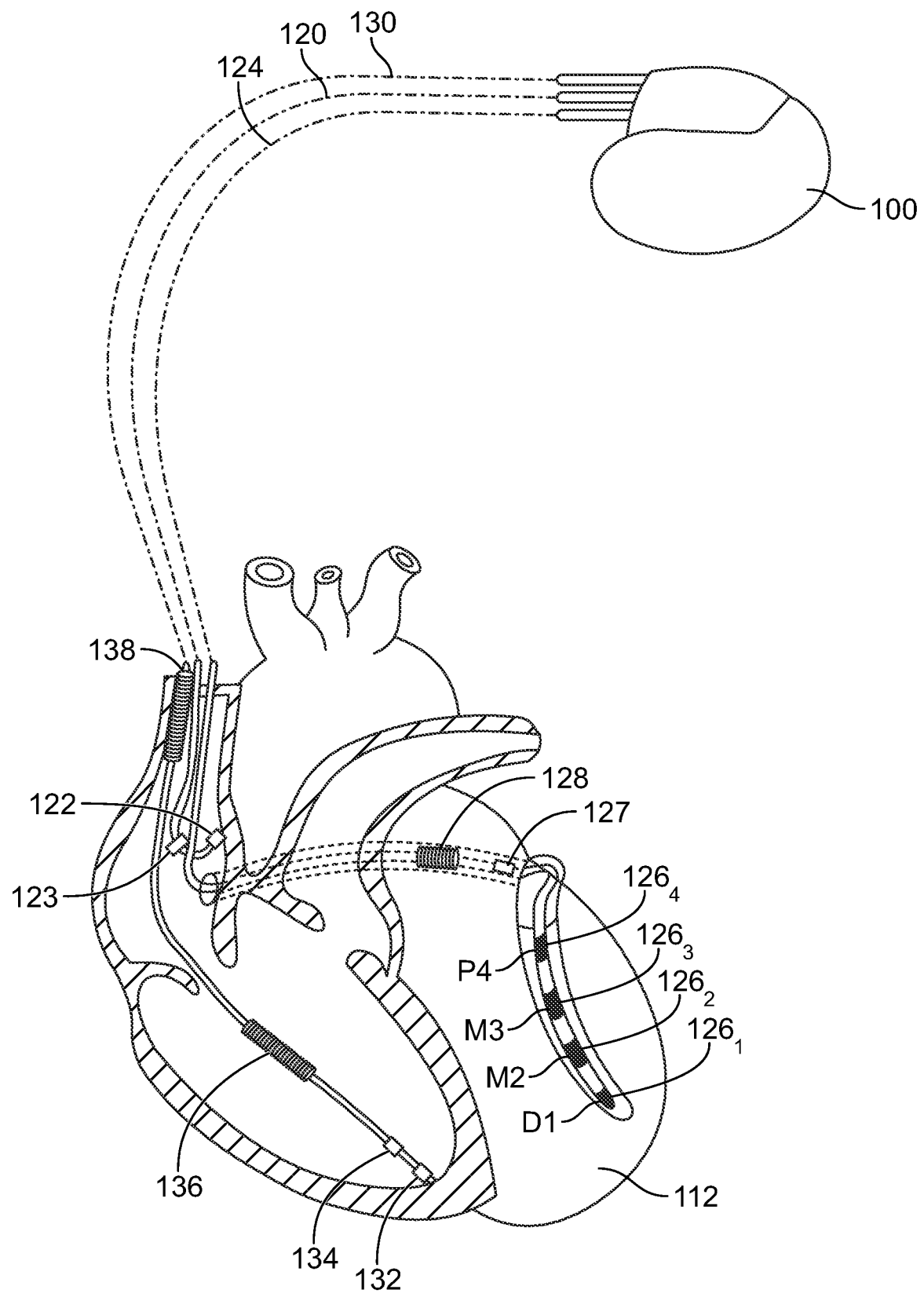
FIG. 1 illustrates an exemplary IMD formed in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "pacing/sensing electrode" refers to an electrode that is controlled and utilized by an implantable medical device and/or external programmer to perform both delivery of pacing pulses at a site and sensing of cardiac signals at the same site.

The term "non-pacing/sensing electrode" refers to an electrode that is controlled and utilized only for sensing operations. The non-pacing-sensing electrode may be on a lead coupled to a lead-based implantable medical device and/or external programmer to perform sensing of cardiac signals at the corresponding site and is not controlled or utilized to deliver pacing pulses. The non-pacing-sensing electrode may be on a leadless implantable medical device that uses the electrode to perform sensing of cardiac signals at the corresponding site and does not use the electrode to deliver pacing pulses.

Embodiments may be implemented in connection with one or more implantable medical devices (IMDs). Non-limiting examples of IMDs include one or more of implantable lead-based or leadless therapy devices. For example, the IMD may represent a pacemaker, cardioverter, cardiac rhythm management device, defibrillator, whether lead-based or leadless. For example, the IMD may include one or more structural and/or functional aspects of the device(s) described in U.S. Pat. No. 9,216,285 "Leadless Implantable Medical Device Having Removable And Fixed Components"; U.S. Pat. No. 8,442,634 "Systems and Methods for Controlling Ventricular Pacing in Patients with Long Inter-Atrial Conduction Delays"; and/or U.S. Pat. No. 8,923,965 "Systems and Methods for Optimizing AV/VV Pacing Delays Using Combined IEGM/Impedance-Based Techniques for use with Implantable Medical Devices"; U.S. Patent Application Publication 2014/0039333 "Systems and Methods for Detecting Mechanical Dyssynchrony and Stroke Volume for use with an Implantable Medical Device Employing a Multi-Pole Left Ventricular Lead", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference in their entireties.

Embodiments may be implemented in connection with one or more of the therapy management systems and methods described in U.S. Pat. No. 7,248,925 "System And Method For Determining Optimum Atrial-Ventricular Delay Based On Intrinsic Conduction Delays", Issuing Jul. 24, 2007, U.S. Pat. No. 7,643,878 "System And Method For Determining Atrial-Ventricular Pacing Delay Based On Atrial Depolarization", Issuing Jan. 5, 2010, U.S. Pat. No. 7,761,160 "System And Method For Determining Atrial-Ventricular Pacing Delay Based On Atrial Repolarization", which are hereby incorporated by reference in their entireties.

FIG. 1 illustrates an exemplary IMD 100 formed in accordance with embodiments herein. The IMD 100 is shown in electrical communication with a heart 112 by way of a right atrial lead 120 having an atrial tip electrode 122 and an atrial ring electrode 123 implanted in the atrial appendage. The IMD 100 is also in electrical communication with the heart by way of a right ventricular lead 130 having, in this embodiment, a ventricular tip electrode 132, a right ventricular ring electrode 134, a right ventricular (RV) coil electrode 136, and a superior vena cava (SVC) coil electrode 138. Typically, the right ventricular lead 130 is transvenously inserted into the heart so as to place the RV coil electrode 136 in the right ventricular apex, and the SVC coil electrode 138 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, IMD 100 is coupled to a multi-pole LV lead 124 designed for placement in the "CS region" via the CS OS for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 124 is designed to receive atrial and ventricular cardiac signals and to deliver left ventricular pacing therapy using a set of four left ventricular electrodes $126_1$, $126_2$, $126_3$, and $126_4$ (thereby providing a quadripole lead), left atrial pacing therapy using at least a left atrial ring electrode 127, and shocking therapy using at least a left atrial coil electrode 128 implanted on or near the left atrium. In other examples, more or fewer LV electrodes are provided. Although only three leads are shown, it should be understood that additional leads (with one or more pacing, sensing and/or shocking electrodes) might be used and/or additional electrodes might be provided on the leads already shown, such as additional electrodes on the RV lead.

Implantable Medical Device

Figure 2:
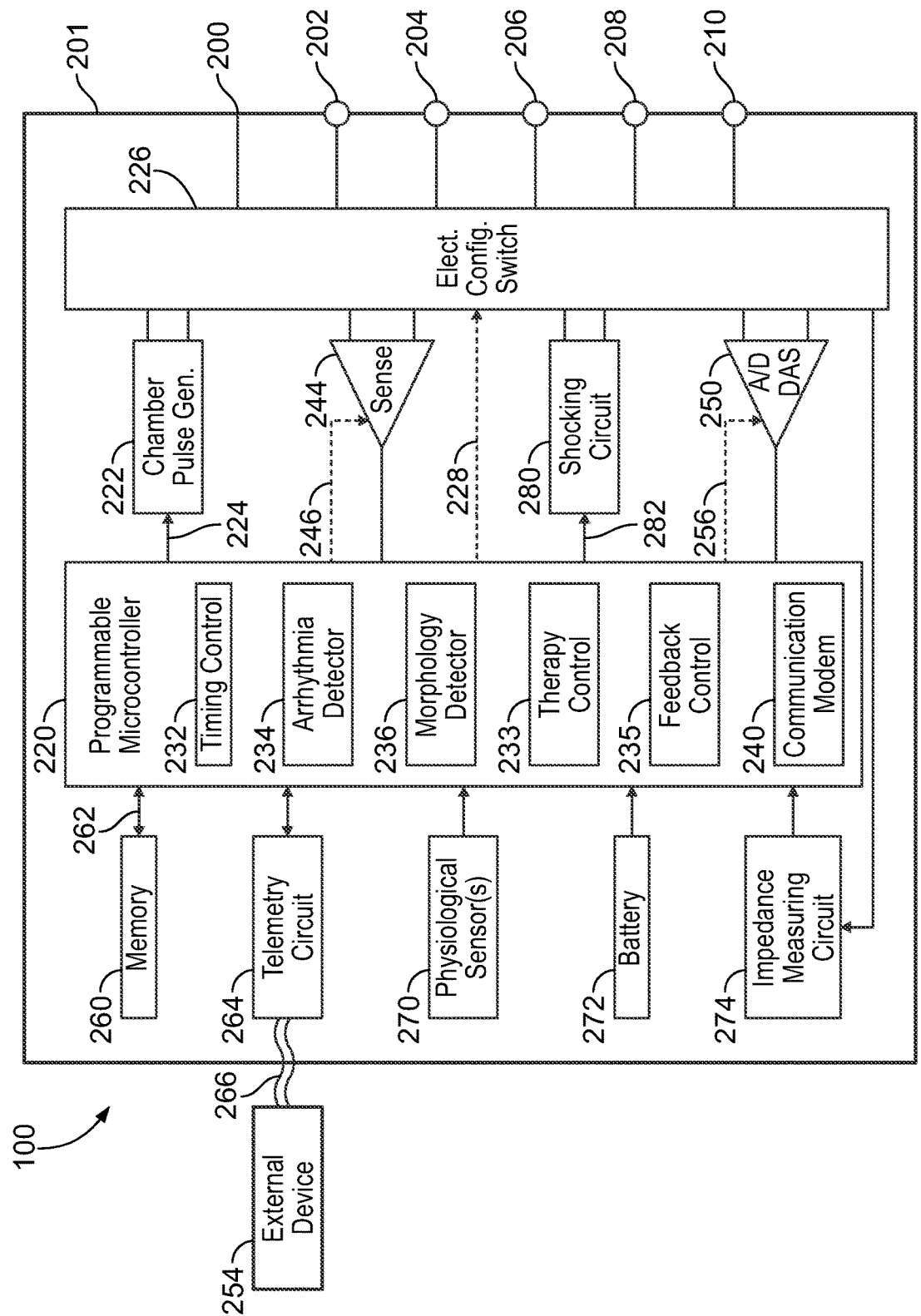
FIG. 2 shows a block diagram of an exemplary IMD that is implanted into the patient as part of the implantable cardiac system in accordance with embodiments herein.

FIG. 2 shows a block diagram of an exemplary IMD 100 that is implanted into the patient as part of the implantable cardiac system. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing. As described herein, the IMD 100 is configured to provide SRAT pacing therapy without pacing the RV.

The IMD 100 has a housing 201 to hold the electronic/computing components. The housing 201 (which is often referred to as the "can", "case", "encasing", or "case electrode") may be programmably selected to act as the return electrode for certain stimulus modes. Housing 201 further includes a connector (not shown) with a plurality of terminals, a portion of which are designated as terminals 202, 204, 206, 208, and 210. The terminals may be connected to electrodes that are located in various locations within and about the heart. For example, the terminals may include: a terminal 202 to be coupled to an first electrode (e.g., a tip electrode) located in a first chamber; a terminal 204 to be coupled to a second electrode (e.g., tip electrode) located in a second chamber; a terminal 206 to be coupled to an electrode (e.g., ring) located in the first chamber; a terminal 208 to be coupled to an electrode located (e.g., ring electrode) in the second chamber; and a terminal 210 to be coupled to an electrode (e.g., coil) located in the SVC. The type and location of each electrode may vary. For example, the electrodes may include various combinations of ring, tip, coil and shocking electrodes and the like. It is understood that more or fewer terminals may be utilized. With reference to FIG. 1, the housing 201 includes at least a number of terminals corresponding to the number of electrodes provided on leads 120, 124 and 130. For example, terminals are provided to connect to the LV electrodes $126_1$-$126_4$.

The IMD 100 includes a programmable microcontroller 220 that controls various operations of the IMD 100, including cardiac monitoring and stimulation therapy. Microcontroller 220 includes a microprocessor (or equivalent control circuitry), RAM and/or ROM memory, logic and timing circuitry, state machine circuitry, and I/O circuitry.

The IMD 100 further includes one or more pulse generators 222 that generates stimulation pulses for delivery by one or more electrodes coupled thereto. The pulse generator 222 is controlled by the microcontroller 220 via control signal 224. The pulse generator 222 is coupled to the select electrode(s) via an electrode configuration switch 226, which includes multiple switches for connecting the desired electrodes to the appropriate I/O circuits, thereby facilitating electrode programmability. The switch 226 is controlled by a control signal 228 from the microcontroller 220.

In the example of FIG. 2, a single pulse generator 222 is illustrated. Optionally, the IMD 100 may include multiple pulse generators, similar to pulse generator 222, where each pulse generator is coupled to one or more electrodes and controlled by the microcontroller 220 to deliver select stimulus pulse(s) to the corresponding one or more electrodes.

Microcontroller 220 is illustrated to include timing control circuitry 232 to control the timing of the stimulation pulses (e.g., pacing rate, atrio-ventricular (AV) delay, atrial interconduction (A-A) delay, or ventricular interconduction (V-V) delay, etc.). The timing control circuitry 232 may also be used for the timing of refractory periods, blanking intervals, noise detection windows, evoked response windows, alert intervals, marker channel timing, and so on. Microcontroller 220 also has an arrhythmia detector 234 for detecting arrhythmia conditions and a morphology detector 236 to review and analyze one or more features of the morphology of cardiac signals.

The microcontroller 220 includes a septum to RV activation time (SRAT) therapy control circuitry 233 to implement the processes described herein for controlling an LV univentricular pacing therapy. The SRAT therapy control circuitry 233 measures activation times between the multiple LV sites and the RV site based on the CA signals; programs an order of activation for the multiple LV sites based on the activation times; identifies an RV activation time and a septum activation time based on the CA signals; calculates a septum to RV activation time (SRAT) based on the RV and septum activation times; and programs an $AV_{SRAT}$ delay based on the SRAT. The SRAT therapy control circuitry 233 manages the SRAT pacing therapy based on the $AV_{SRAT}$ delay.

The memory 260 is configured to store $AV_{SRAT}$ delay that is set by the SRAT therapy control circuitry 233.

The microcontroller 220 also includes $AV_{SRAT}$ feedback control circuitry 235 to implement the processes described in connection with feedback control to monitor the SRAT pacing therapy and adjust the $AV_{SRAT}$ delay. Although not shown, the microcontroller 220 may further include other dedicated circuitry and/or firmware/software components that assist in monitoring various conditions of the patient's heart and managing pacing therapies. The $AV_{SRAT}$ feedback control circuitry 235 manages feedback to confirm the SRAT pacing therapy. The $AV_{SRAT}$ feedback control circuitry 235 uses at least one of QRS related feedback, mechanical di-synchrony related feedback or stroke volume surrogate related feedback. For example, the $AV_{SRAT}$ feedback control circuitry 235 may analyze a paced QRS width in connection with multiple $AV_{SRAT}$ delays, and select an $AV_{SRAT}$ delay corresponding to the paced QRS width having a criteria of interest. Optionally, the $AV_{SRAT}$ feedback control circuitry 235 may analyze a contractility time delay in connection with multiple $AV_{SRAT}$ delays, and select an $AV_{SRAT}$ delay corresponding to the contractility time delay having a criteria of interest. Optionally, the $AV_{SRAT}$ feedback control circuitry 235 may analyze a stroke volume impedance in connection with multiple $AV_{SRAT}$ delays, and select an $AV_{SRAT}$ delay corresponding to the stroke volume impedance having a criteria of interest.

The IMD 100 is further equipped with a communication modem (modulator/demodulator) 240 to enable wireless communication with other devices, implanted devices and/or external devices. In one implementation, the communication modem 240 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The communication modem 240 may be implemented in hardware as part of the microcontroller 220, or as software/firmware instructions programmed into and executed by the microcontroller 220. Alternatively, the modem 240 may reside separately from the microcontroller as a standalone component.

The IMD 100 includes sensing circuitry 244 selectively coupled to one or more electrodes that perform sensing operations, through the switch 226 to detect the presence of cardiac activity in the right chambers of the heart. The sensing circuitry 244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the IMD 100 to sense low amplitude signal characteristics of atrial fibrillation. Switch 226 determines the sensing polarity of the cardiac signal by selectively closing the appropriate switches. In this way, the clinician may program the sensing polarity independent of the stimulation polarity. The sensing circuitry 244 defines first and second sensing channels corresponding to first and second sensing vectors, respectively. As explained herein, the first sensing channel may correspond to a RV local sensing channel, such as between the RV tip and RV ring electrodes. The second sensing channel corresponds to an intraventricular sensing channel (or chamber to chamber sensing channel), such as between one or more LV electrodes and one or more RV electrodes.

The output of the sensing circuitry 244 is connected to the microcontroller 220 which, in turn, triggers or inhibits the pulse generator 222 in response to the absence or presence of cardiac activity. The sensing circuitry 244 receives a control signal 246 from the microcontroller 220 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 244 is illustrated. Optionally, the IMD 100 may include multiple sensing circuit, similar to sensing circuit 244, where each sensing circuit is coupled to one or more electrodes and controlled by the microcontroller 220 to sense electrical activity detected at the corresponding one or more electrodes. The sensing circuit 244 may operate in a unipolar sensing configuration or in a bipolar sensing configuration.

The IMD 100 further includes an analog-to-digital (ND) data acquisition system (DAS) 250 coupled to one or more electrodes via the switch 226 to sample cardiac signals across any pair of desired electrodes. The data acquisition system 250 is configured to acquire intracardiac electrogram signals, convert the raw analog data into digital data, and store the digital data for later processing and/or telemetric transmission to an external device 254 (e.g., a programmer, local transceiver, or a diagnostic system analyzer). The data acquisition system 250 is controlled by a control signal 256 from the microcontroller 220.

The microcontroller 220 is coupled to a memory 260 by a suitable data/address bus 262. The programmable operating parameters used by the microcontroller 220 are stored in memory 260 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart within each respective tier of therapy.

The operating parameters of the IMD 100 may be non-invasively programmed into the memory 260 through a telemetry circuit 264 in telemetric communication via communication link 266 with the external device 254. The telemetry circuit 264 allows intracardiac electrograms and status information relating to the operation of the IMD 100 (as contained in the microcontroller 220 or memory 260) to be sent to the external device 254 through the established communication link 266.

The IMD 100 can further include magnet detection circuitry (not shown), coupled to the microcontroller 220, to detect when a magnet is placed over the unit. A magnet may be used by a clinician to perform various test functions of the unit 200 and/or to signal the microcontroller 220 that the external programmer 254 is in place to receive or transmit data to the microcontroller 220 through the telemetry circuits 264.

The IMD 100 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. The microcontroller 220 responds by adjusting the various pacing parameters (such as rate, AV Delay, V-V Delay, etc.) at which the atrial and ventricular pacing pulses are administered. While shown as being included within the unit 200, the physiologic sensor(s) 270 may be external to the unit 200, yet still be implanted within or carried by the patient. Examples of physiologic sensors might include sensors that, for example, sense respiration rate, pH of blood, ventricular gradient, activity, position/posture, minute ventilation (MV), and so forth.

A battery 272 provides operating power to all of the components in the IMD 100. The battery 272 is capable of operating at low current drains for long periods of time and is capable of providing high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the unit 200 employs lithium/silver vanadium oxide batteries.

The IMD 100 further includes an impedance measuring circuit 274 that is enabled by the microcontroller 220 via a control signal 280. As explained herein, the impedance measuring circuit 274 may be utilized in a feedback loop to collect cardiogenic impedance signals along one or more impedance vectors while delivering an SRAT pacing therapy having an $AV_{SRAT}$ delay defined in accordance with embodiments herein. One or more of the impedance vectors may be utilized. For example, impedance vectors may be defined between an RV electrode and a corresponding LV electrode, between and RV coil electrode and a housing/can of the IMD, and/or a combination of one or more RV electrode, one or more LV electrode and the housing/can of the IMD. The cardiogenic impedance signals may be utilized to determine contractility time delays associated with different LV sites and/or a surrogate for stroke volume. For example, the cardiogenic impedance signals may be collected as described in U.S. Pat. No. 8,923,965 "Systems and Methods for Optimizing AV/VV Pacing Delays Using Combined IEGM/Impedance-Based Techniques for use with Implantable Medical Devices"; and U.S. Patent Application Publication 2014/0039333 "Systems and Methods for Detecting Mechanical Dyssynchrony and Stroke Volume for use with an Implantable Medical Device Employing a Multi-Pole Left Ventricular Lead", which are incorporated herein by reference in their entirety.

The impedance measuring circuit 274 may also be used for: performing lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 274 is coupled to the switch 226 so that any desired electrode may be used.

The IMD 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 211 to 40 joules), as controlled by the microcontroller 220. Such shocking pulses are applied to the patient's heart 2108 through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

Figure 3:
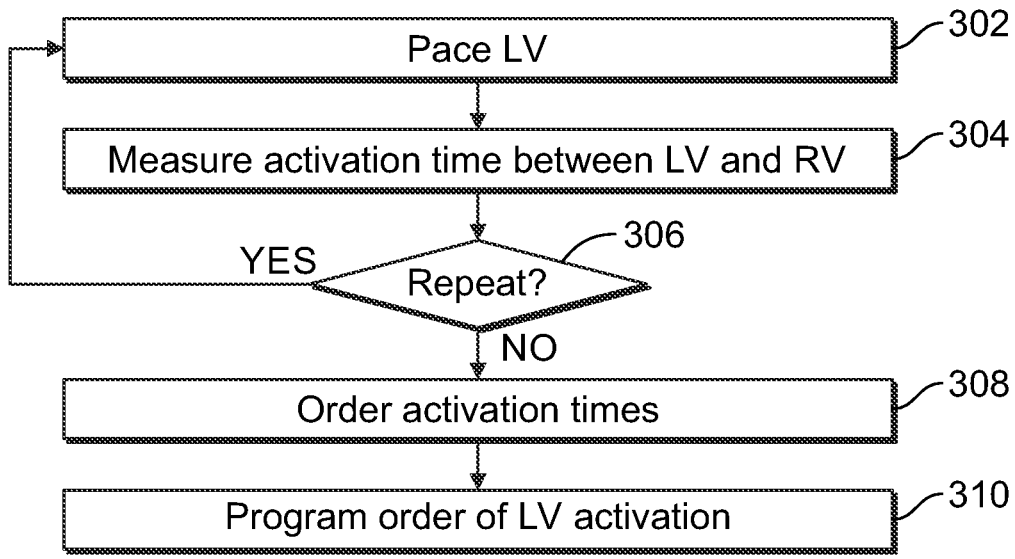
FIG. 3 illustrates a process for managing a timing for activation between LV stimulation sites in accordance with embodiments herein.

FIG. 3 illustrates a process for managing a timing for activation between LV stimulation sites in accordance with embodiments herein. The process of FIG. 3 may be implemented under the control of one or more processors in the IMD and/or one or more processors of an external programmer. At 302, the one or more processors direct delivery of a stimulation pacing pulse at a first LV site, such as LV1. At 304, the one or more processors monitor an RV sensing site for cardiac activity resulting from the pacing pulse delivered at the first LV site. For example, the RV sensing site may correspond to an RV tip or coil electrode. When activation is sensed at the RV sensing site, the processors determine a measured activation time between the LV-RV sites. At 306, the one or more processors determine whether to repeat the measurement of the activation time for a next LV sensing site. If so, flow returns to 302. Otherwise, flow continues to 308. When flow returns to 302, a stimulation pacing pulse is delivered at a next LV site (at 302). The RV sensing site is again monitored for measured activity and a measured activity time is determined between the second LV pacing site and the RV sensing site. The operations at 302-306 are repeated for each LV pacing site.

At 308, the processors order the activation times, such as from the longest to the shortest activation time. At 310, the one or more processors program an order of activation for the LV pacing sites based on the activation times ordered at 308. For example, when the proximal LV electrode is determined to have the longest activation time, the proximal LV electrode may be programmed to deliver a pacing pulse first relative to other LV pacing sites. When the distal LV electrode is determined to have the shortest activation time, the distal LV electrode reprogrammed to deliver a pacing pulse last, relative to the other LV pacing sites. Optionally, more than one LV electrode may be programmed to simultaneously deliver pacing pulses.

Figure 4:
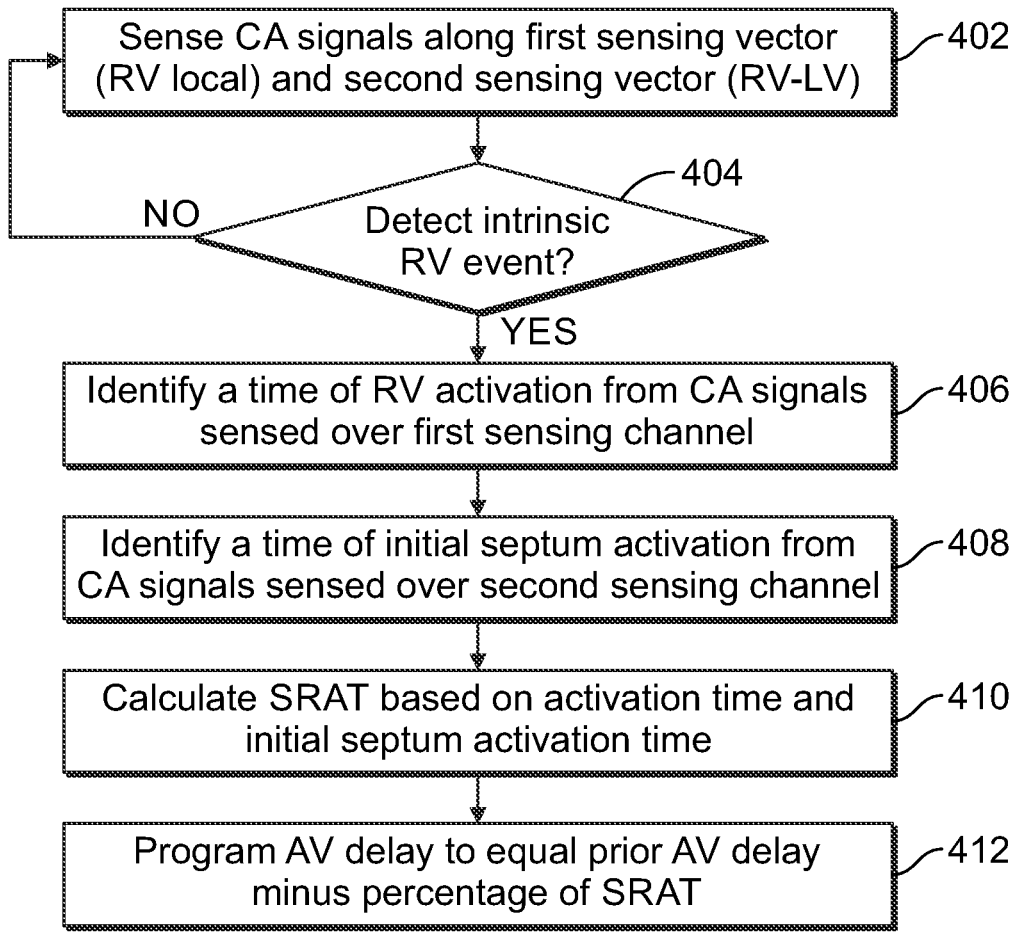
FIG. 4 illustrates a process for managing an intraventricular activation timing between LV and RV stimulation sites in accordance with embodiments herein.

FIG. 4 illustrates a process for managing an intraventricular activation timing between LV and RV stimulation sites in accordance with embodiments herein. The process of FIG. 4 may be implemented under the control of one or more processors in the IMD and/or one or more processors of an external programmer. At 402, the one or more processors collect cardiac activity along one or more sensing vectors (corresponding to one or more sensing channels). For example, cardiac activity may be collected along a first sensing vector, corresponding to a local RV sensing vector, between RV electrodes (e.g. between the RV tip electrode and RV coil electrode). Cardiac activity may be collected along a second sensing vector, corresponding to an intraventricular sensing vector, between an RV electrode and an LV electrode. The first and second sensing vectors correspond to first and second sensing channels that may be defined to have different sensing characteristics. The cardiac activity signals are continuously recorded, such as in a circular buffer, for a desired amount of time (e.g. a 300-500 ms sampling window).

At 404, the one or more processors determine whether onset of an intrinsic RV event was detected. If not, flow returns to 402 where the process continues to collect CA signals over the first and second sensing vectors. At 404, when the processors identify onset of an intrinsic RV event, flow moves to 406. The determination at 404 may be based on a comparison of the CA signals collected over the first sensing vector (e.g. between the RV tip electrode and RV coil electrode) to a threshold (e.g. an R-wave peaked threshold).

At 406, the one or more processors identify the time of RV activation. For example, the RV activation time $T_{RV}$ may correspond to a peak of an R-wave, in a QRS complex, as detected over an RV sensing channel. At 408, the one or more processors analyze the cardiac activity signals sensed over the second sensing channel to identify a time of initial septum activation. For example, the septum activation time $T_{SEP}$ may correspond to a point in time at which the CA signals sensed over the second sensing channel begin to rise above a baseline/neutral voltage level. The septum activation time represents an onset of a Q-wave in a QRS complex. The second sensing channel corresponds to a second sensing vector, also referred to as an intraventricular (or RV-LV cross chamber) vector between one or more LV electrodes and one or more RV electrode. For example, the RV-LV cross chamber vector make be between the distal LV electrode and the RV tip electrode. It is recognized that other combinations of RV and LV electrodes may be utilized to define the cross chamber sensing vector.

At 410, the one or more processors calculate a septum to RV activation time (SRAT) corresponding to the interval between the septum activation time $T_{SEP}$ in the RV activation time $T_{RV}$.

At 412, the one or more processors set/program an AV delay by reducing the AV delay by an amount to correspond to a percentage of the SRAT. For example, the SRAT may be determined to be 40 ms. A percentage of the SRAT may correspond to 50% or 20 ms. The processors may set/program the AV delay (also referred to as an $AV_{SRAT}$ delay) by reducing a previously set/programmed AV delay by the percentage of the SRAT (e.g. prior AV delay −20 ms).

While various embodiments are described herein in connection with a lead based implantable medical device that is coupled to one or more transveous leads, it is recognized that embodiments herein may also be implanted in connection with a combination of leadless devices and/or lead based and leadless devices. For example, a left ventricular lead may be implanted with electrodes positioned at various LV sites (as indicated in FIG. 1, while a separate leadless device is implanted in the RV. The leadless RV device may communicate with the lead based IMD coupled to the LV lead to analyze CA signals collected by the lead based and leadless devices, identify the RV activation time and septum activation time, calculate the SRAT and $AV_{SRAT}$ delay based on the SRAT as explained herein.

In accordance with at least one embodiment, the operations described in connection with FIG. 4 may be divided between operation performed by an implantable medical device and operations performed by an external device. For example, the implantable medical device and an external device are configured to configured to wirelessly communicate with one another. The implantable medical device is coupled to the electrodes (e.g. in a lead-based device or a leadless device) and configured to collect the CA signals over first and second sensing channels. The IMD is configured to transmit the CA signals to the external device. The external device including one or more processors configured to: identify the RV activation time and the septum activation time based on the CA signals; calculate the SRAT based on the RV and septum activation times; calculate the $AV_{SRAT}$ delay based on the SRAT; and wirelessly transmit the $AV_{SRAT}$ delay to the implantable medical device. The implantable medical device utilizes the $AV_{SRAT}$ delay in connection with delivering therapy.

Figure 5:
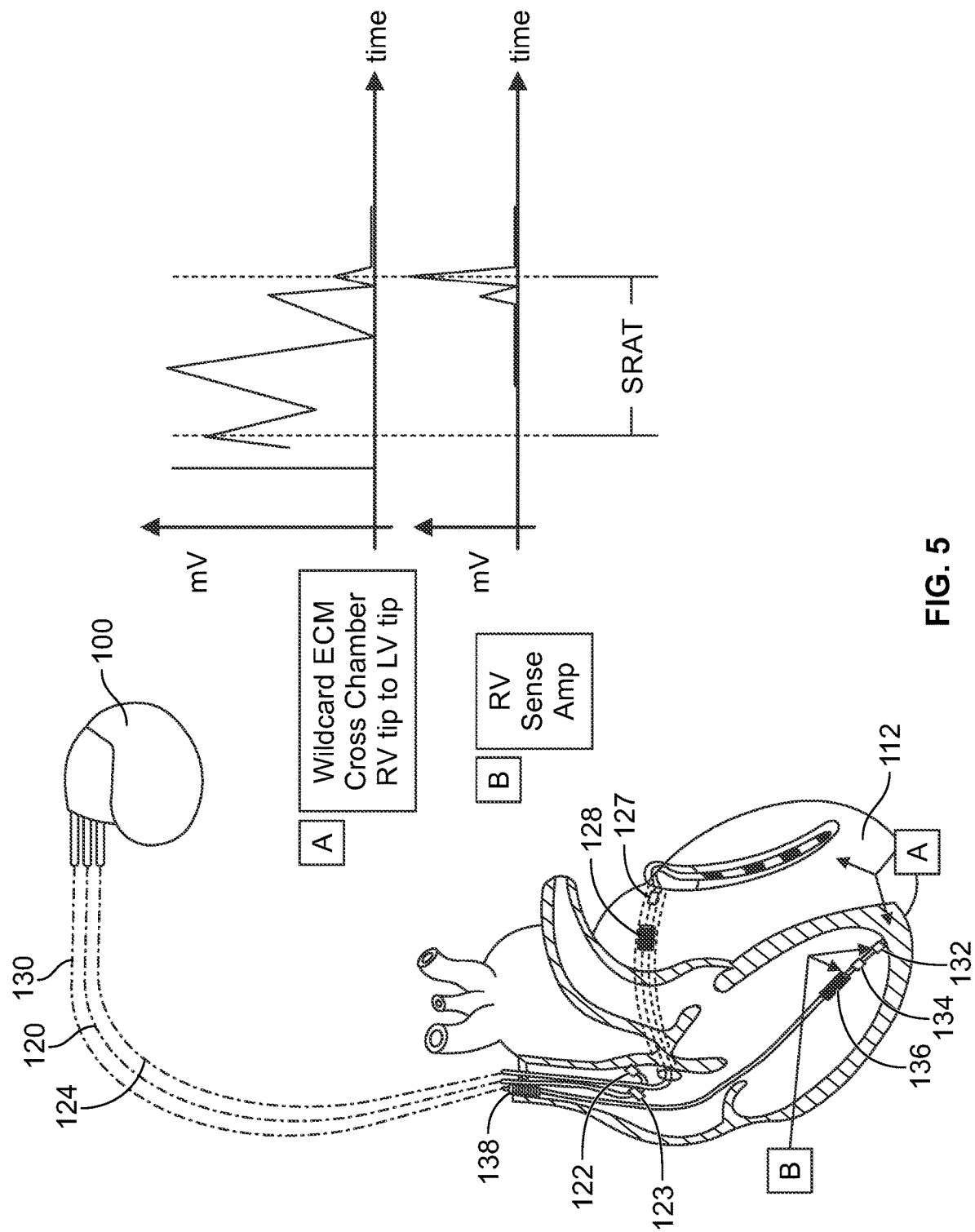
FIG. 5 illustrates a graphical representation of the conduction timing between the CA signals sensed over first and second sensing channels.

FIG. 5 illustrates a graphical representation of the conduction timing between the CA signals sensed over first and second sensing channels. The first sensing channel is designated as B, corresponding to an RV sensing channel between the RV tip and coil electrodes. The sensing circuitry for the RV sensing channel is configured to have a sensitivity to detect local RV events (e.g. the R-wave). The second sensing channel is designated as A, corresponding to an intraventricular or cross-chamber sensing channel between a distal LV electrode and the RV tip electrode. The sensing circuitry corresponding to the second sensing channel is configured to detect intrinsic activity traveling along the intraventricular septum. As noted in FIG. 5, and onset of activation of the septum is detected over the second sensing channel A, while a peak of the R-wave is detected over the first sensing channel B, with the difference therebetween corresponding to the SRAT. The CA signals sensed over the first and second sensing channels are analyzed in connection with the operations of FIG. 4 to calculate the SRAT and adjust the $AV_{SRAT}$ delay accordingly.

Figure 6:
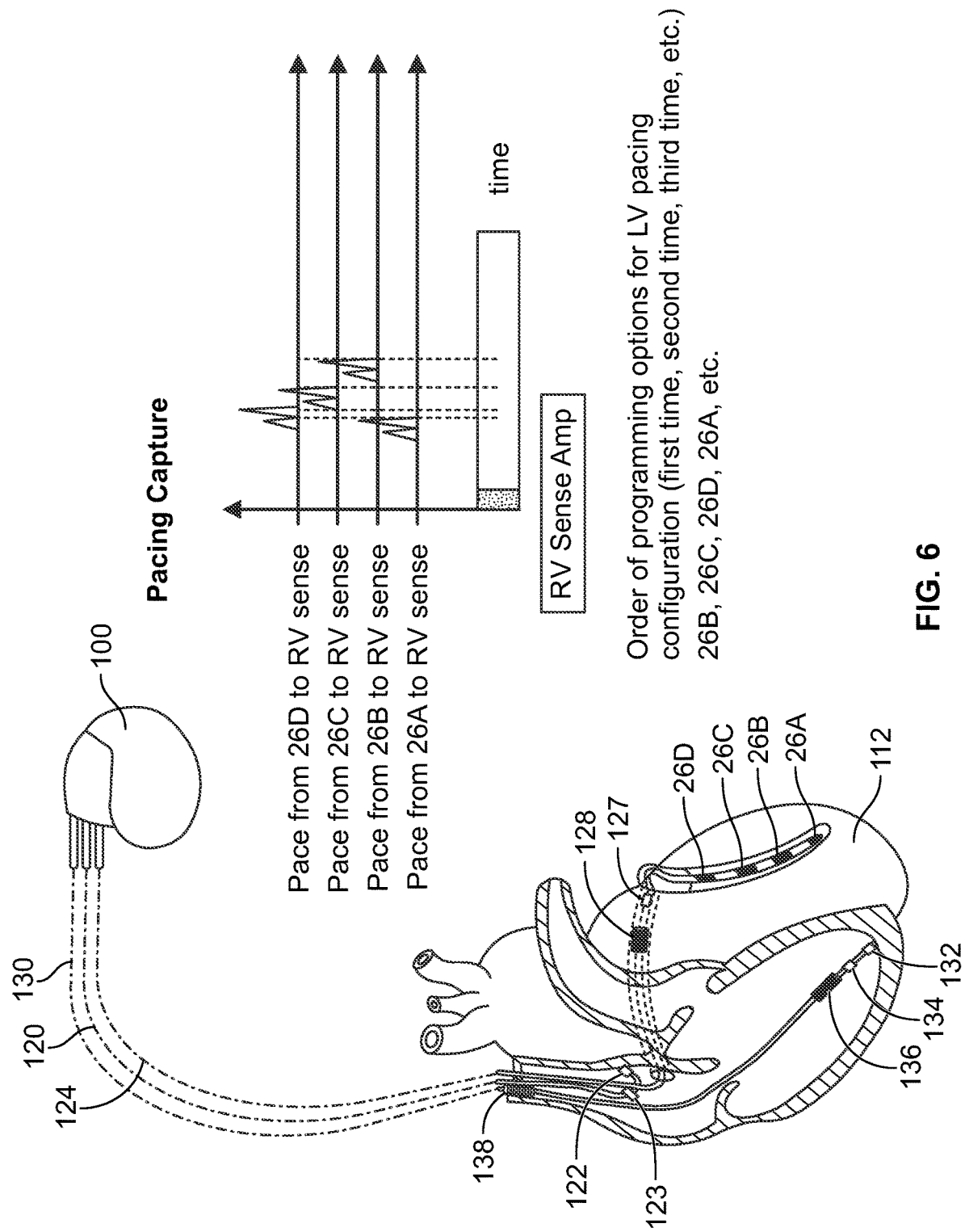
FIG. 6 illustrates a graphical representation of the activation timing measured between an RV site and multiple LV sites.

FIG. 6 illustrates a graphical representation of the activation timing measured between an RV site and multiple LV sites. As explained above in connection with FIG. 3, a stimulation pulse is delivered at a first LV site, and an activation time is measured as the time between delivery of the stimulus at the first LV site and detection of a corresponding intrinsic event at an RV site. The foregoing operation is repeated in connection with each LV site. In the example of FIG. 6, the activation time associated with LV electrode 26B is the longest, followed next by the activation time associated with LV electrode 26C, followed next by the activation time associated with LV electrode 26D, and last lay followed by the activation time associated with the LV electrode 26A. In the foregoing example, the order of activation assigned to the LV electrodes would be LV electrode 26B, then LV electrode 26C, then followed by LV electrode 26D, and followed by LV electrode 26A.

Figure 7:
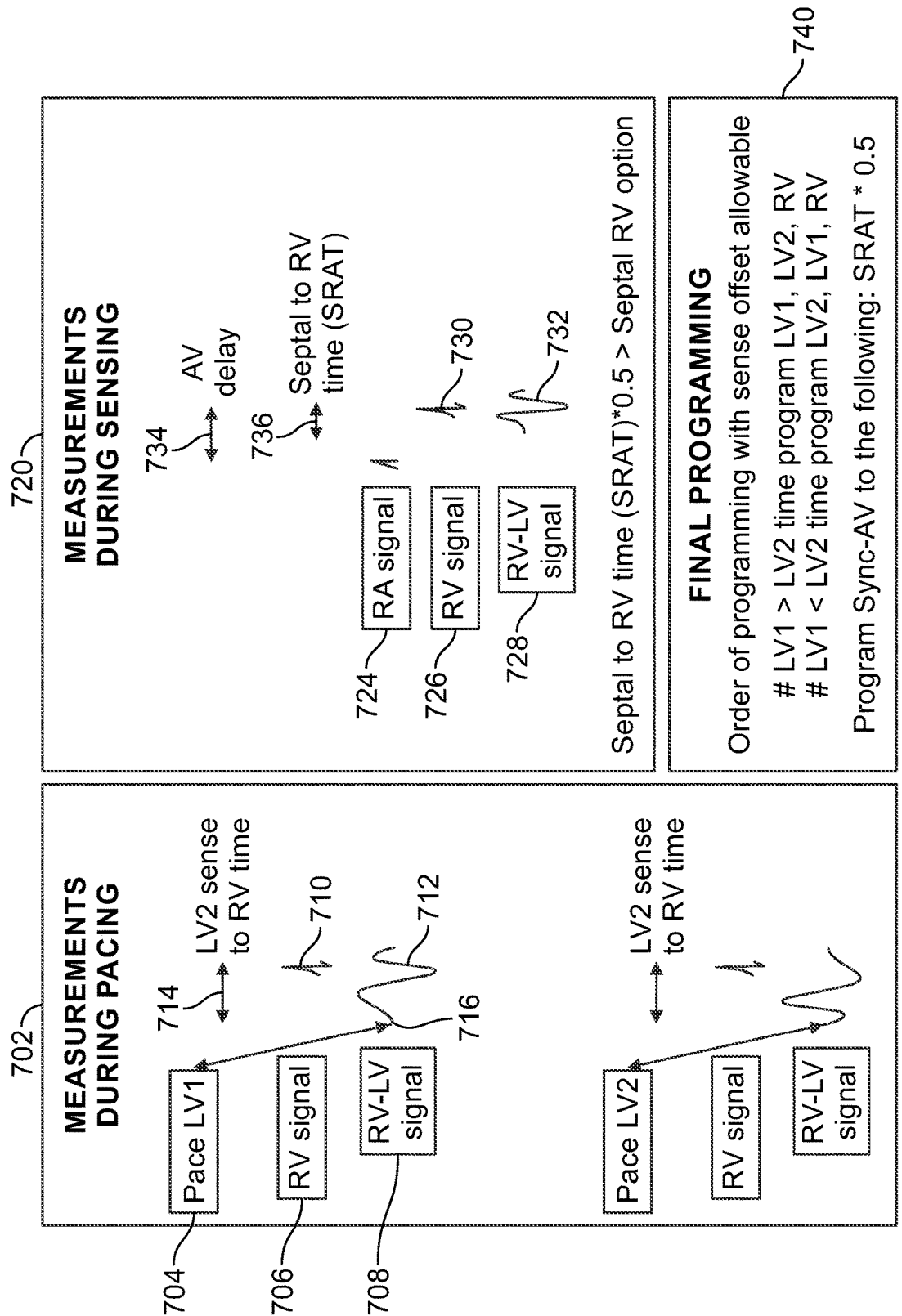
FIG. 7 illustrates examples of timings associated with measurements during paced events and measurements during sensed events.

FIG. 7 illustrates examples of timings associated with measurements during paced events and measurements during sensed events. In panel 702, a paced event 704 is delivered at LV1. The RV local sensing channel 706 between the RV tip and ring electrodes detect a corresponding sensed event at 710, while the cross-chamber sensing channel 708 between an LV electrode and an RV electrode detect a corresponding sensed event at 712. The activation time 714 is determined as the timer interval between the paced event 716 and the sensed event 710. Panel 702 also illustrates a timing associated with a paced event delivered at a second electrode LV2, along with the sensed intrinsic RV event and associated activation time.

Panel 720 illustrates examples of timings associated with measurements during an intrinsic RA event 724 and measurements during sensed events. In panel 720, the intrinsic RA event 724 is detected. The RV local sensing channel 726 between the RV tip and ring electrodes detect a corresponding sensed event at 730, while the cross-chamber sensing channel 728 between an LV electrode and an RV electrode detect a corresponding sensed event at 732. The activation time 734 is determined as the timer interval between the intrinsic event 724 and the sensed event 730. Panel 720 also illustrates a timing associated with the SRAT 736 between the onset of the Q-wave and a peak of the R-wave.

Panel 740 illustrates an example of a final programming that may result based on the measurements obtained from the CA signals in panels 702 and 720.

Optionally, SRAT based AV delay may be confirmed through QRS related feedback in accordance with embodiments herein. For example, the one or more processors may deliver an SRAT therapy that utilizes an $AV_{SRAT}$ delay calculated in accordance with embodiments. The one or more processors measure and save a paced QRS width corresponding to the width of the QRS complex in connection with a paced event. The one or more processors determine whether to continue delivering the SRAT pacing therapy and measuring the paced QRS width. For example, a select number of paced events may be delivered and a select number of paced QRS widths may be measured and saved before it is desirable to continue the process. The paced QRS widths measured and saved may be combined to form an average or separately stored for individual analysis in connection here with. The one or more processors determine whether to adjust to the $AV_{SRAT}$ delay. When it is desirable to adjust the $AV_{SRAT}$ delay, the $AV_{SRAT}$ delay is adjusted by a predetermined increment, such as a programmed amount or automatically determined amount. For example, the $AV_{SRAT}$ delay may be increased or decreased by the corresponding increment during each iteration. Next, the one or more processors compare the saved paced QRS widths to determine a desired one of the paced QRS widths that has criteria of interest. For example, the criteria of interest may correspond to the shortest QRS width. Optionally, the criteria of interest may correspond to a QRS width within a desired length. Additional or alternative criteria of interest may be applied when selecting the paced QRS width. The one or more processors select the QRS width that has the criteria of interest and determine the corresponding associated $AV_{SRAT}$ delay. The one or more processors update the SRAT pacing therapy to use the $AV_{SRAT}$ delay determined.

In accordance herewith, a feedback loop is provided to monitor physiologic response to the programmed $AV_{SRAT}$ delay parameter for an SRAT pacing therapy. Additionally or alternatively, additional parameters may be adjusted and analyzed in connection with utilizing the feedback loop to review the physiologic response to the SRAT pacing therapy.

Optionally, a process may be utilized for confirming an SRAT pacing therapy through the use of mechanical dyssynchrony related feedback in accordance with embodiments herein. The one or more processors deliver an SRAT therapy that utilizes an $AV_{SRAT}$ delay calculated in accordance with embodiments herein. The one or more processors measure and save cardiogenic impedance signals along one or more impedance vectors through the LV. For example, an impedance vector may be between an electrode located at an RV site (e.g., an RV coil electrode) and an electrode located at an LV site. Optionally, when electrodes are positioned at multiple LV sites, separate cardiogenic impedance signals may be obtained for impedance vectors associated with each of the LV sites, and/or combinations of the LV sites. For example, the lead may include four LV electrodes (e.g., a proximal electrode, first middle electrode, second middle electrode and distal electrode). First cardiogenic impedance measurements may be obtained along a first impedance vector between the proximal LV electrode and an RV electrode. Second cardiogenic impedance measurements may be obtained along a second impedance vector between the first middle electrode and the RV electrode, while third and fourth cardiogenic impedance measurements may be obtained along a third impedance vector (second middle electrode to RV electrode) and along a fourth impedance vector (distal electrode to RV electrode). Additionally or alternatively, combinations of the LV sites may be combined to form a virtual LV electrode, with the impedance vector extending between the RV electrode and the virtual LV electrode.

The one or more processors analyze a cardiogenic impedance (CI) signal corresponding to the cardiogenic impedance measurements collected along one impedance vector. The processors identify an impedance characteristic of interest from the CI signal. For example, the impedance characteristic of interest (COI) may correspond to a maximum or minimum in the slope of the CI signal over time (e.g., maximum ΔdZ/dt). The one or more processors determine a contractility time delay between a QRS complex COI and the impedance COI. For example, the QRS complex COI may correspond to the peak of the QRS complex, while the impedance COI corresponds to the maximum slope in the CI signal. The contractility time delay between the characteristics of interest is saved. The processor determines whether additional CI signals are to be analyzed.

The one or more processors compare the contractility time delays associated with the different LV electrodes/sites to identify a mechanical dyssynchrony indicator there between. For example, the contractility time delays associated with a different LV electrodes/sites may be analyzed to identify a mean and a standard deviation there between. A large standard deviation may represent a mechanical dyssynchrony indicator as the maximum change in the impedance COI occurs at a different point in time at each of the LV sites. When the LV exhibits mechanical synchrony (or low mechanical dyssynchrony), the impedance COI may be expected to exhibit a maximum ΔdZ/dt at approximately the same point in time for each of the LV sites. While the present example utilizes mean and standard deviation as the measure of differences in the contractility time delays for the different LV electrodes, it is recognized that another timing characteristic may be analyzed additionally or alternatively.

The one or more processors determine whether to adjust to the $AV_{SRAT}$ delay. When it is desirable to adjust the $AV_{SRAT}$, the $AV_{SRAT}$ delay is adjusted by a predetermined increment, such as a programmed amount or automatically determined amount. The operations are repeated in connection with multiple $AV_{SRAT}$ delay, to obtain a collection of $AV_{SRAT}$ delays, each of which has a corresponding mechanical dyssynchrony indicator (e.g., corresponding to a mean and standard deviation in the contractility time delays for the different LV electrodes/sites.

The one or more processors compare the saved mechanical dyssynchrony indicators (MDSI) to determine a desired one of the mechanical dyssynchrony indicators that has a criteria of interest. For example, the criteria of interest may correspond to a minimum standard deviation between the contractility time delays associated with an $AV_{SRAT}$ delay. Optionally, the criteria of interest may correspond to a combination of contractility time delays within a desired range of one another. Additional and alternative criteria of interest may be applied when selecting the mechanical dyssynchrony indicator. The one or more processors select the MDSI that has the criteria of interest and determine the corresponding $AV_{SRAT}$ delay. The one or more processors update the SRAT pacing therapy to use the $AV_{SRAT}$ delay determined.

In accordance herewith, a feedback loop is provided to monitor mechanical dyssynchrony indicators in response to the programmed $AV_{SRAT}$ delay parameter for an SRAT pacing therapy.

External Device

Figure 8:
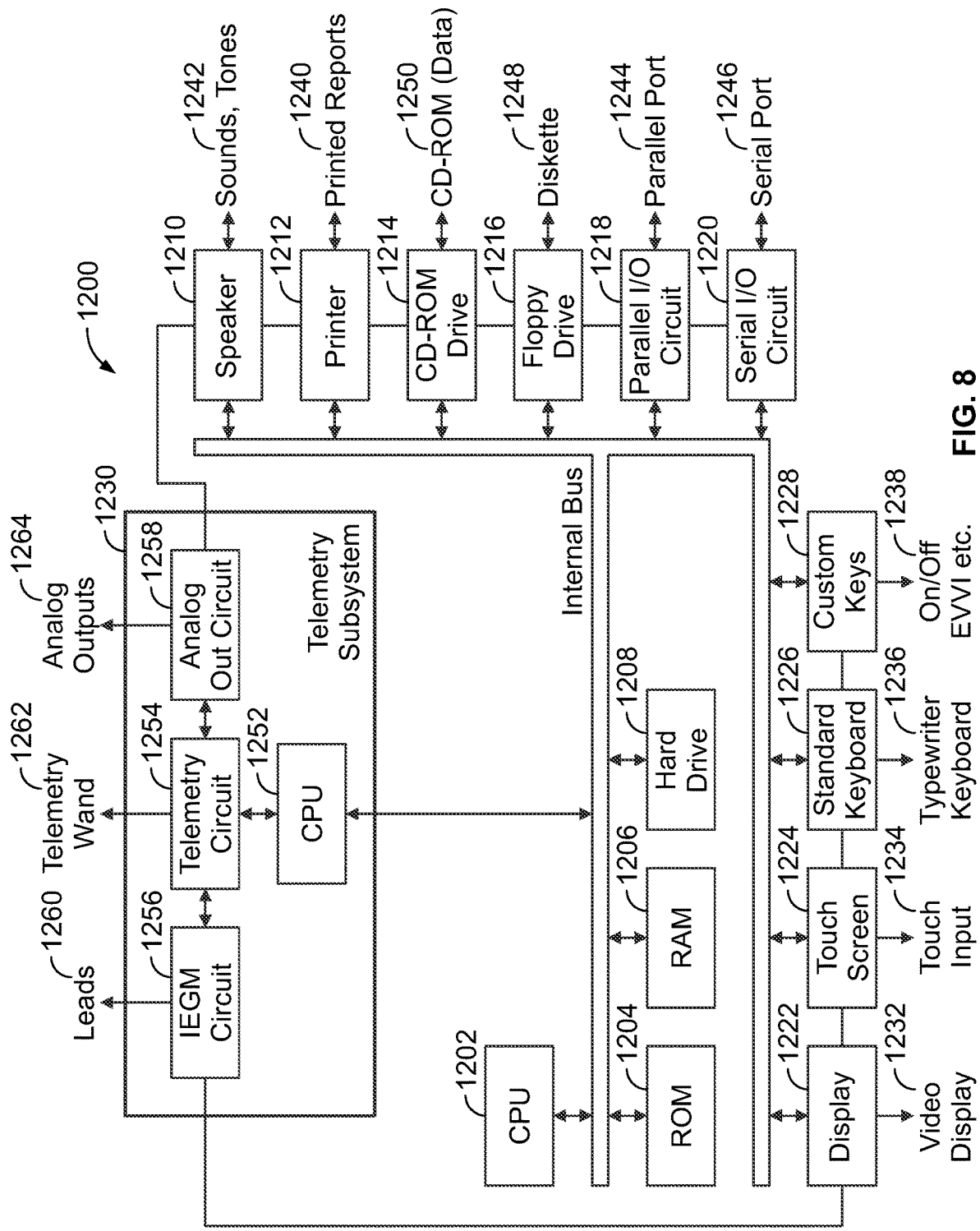
FIG. 8 illustrates a functional block diagram of the external device that is operated in accordance with the processes described herein and to interface with implantable medical devices as described herein.

FIG. 8 illustrates a functional block diagram of the external device 1200 that is operated in accordance with the processes described herein and to interface with implantable medical devices as described herein. The external device 1200 may be a workstation, a portable computer, an IMD programmer, a PDA, a cell phone and the like. The external device 1200 includes an internal bus that connects/interfaces with a Central Processing Unit (CPU) 1202, ROM 1204, RAM 1206, a hard drive 1208, the speaker 1210, a printer 1212, a CD-ROM drive 1214, a floppy drive 1216, a parallel I/O circuit 1218, a serial I/O circuit 1220, the display 1222, a touch screen 1224, a standard keyboard connection 1226, custom keys 1228, and a telemetry subsystem 1230. The internal bus is an address/data bus that transfers information between the various components described herein. The hard drive 1208 may store operational programs as well as data, such as waveform templates and detection thresholds.

The CPU 1202 typically includes a microprocessor, a micro-controller, or equivalent control circuitry, designed specifically to control interfacing with the external device 1200 and with the IMD 100. The CPU 1202 performs the COI measurement process discussed above. The CPU 1202 may include RAM or ROM memory, logic and timing circuitry, state machine circuitry, and I/O circuitry to interface with the IMD 100. The CPU 1202 may implement some or all of the operations of the SRAT therapy control circuitry 233 (FIG. 2) and/or the $AV_{SRAT}$ feedback control circuitry 235 (FIG. 2). The CPU 1202 may implement some or all of the operations of the methods described herein, such as in connection with Figures.

The display 1222 (e.g., may be connected to the video display 1232). The touch screen 1224 may display graphic information relating to the IMD 100. The display 1222 displays various information related to the processes described herein. The touch screen 1224 accepts a user's touch input 1234 when selections are made. The keyboard 1226 (e.g., a typewriter keyboard 1236) allows the user to enter data to the displayed fields, as well as interface with the telemetry subsystem 1230. Furthermore, custom keys 1228 turn on/off 1238 (e.g., EVVI) the external device 1200. The printer 1212 prints copies of reports 1240 for a physician to review or to be placed in a patient file, and speaker 1210 provides an audible warning (e.g., sounds and tones 1242) to the user. The parallel I/O circuit 1218 interfaces with a parallel port 1244. The serial I/O circuit 1220 interfaces with a serial port 1246. The floppy drive 1216 accepts diskettes 1248. Optionally, the floppy drive 1216 may include a USB port or other interface capable of communicating with a USB device such as a memory stick. The CD-ROM drive 1214 accepts CD ROMs 1250.

The telemetry subsystem 1230 includes a central processing unit (CPU) 1252 in electrical communication with a telemetry circuit 1254, which communicates with both an IEGM circuit 1256 and an analog out circuit 1258. The circuit 1256 may be connected to leads 1260. The circuit 1256 is also connected to the implantable leads to receive and process IEGM cardiac signals as discussed above. Optionally, the IEGM cardiac signals sensed by the leads may be collected by the IMD 100 and then transmitted, to the external device 1200, wirelessly to the telemetry subsystem 1230 input.

The telemetry circuit 1254 is connected to a telemetry wand 1262. The analog out circuit 1258 includes communication circuits to communicate with analog outputs 1264. The external device 1200 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 1200 to the IMD 100.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for managing a pacing therapy using an implantable medical device (IMD), the method comprising:
    sensing cardiac activity (CA) signals at electrodes located proximate to multiple left ventricular (LV) sites and a right ventricular (RV) site of the heart;
    measuring activation times between the multiple LV sites and the RV site based on the CA signals;
    identifying an RV activation time and a septum activation time based on the CA signals;
    calculating a septum to RV activation time (SRAT) based on the RV and septum activation times; and
    utilizing one or more processors to program an $AV_{SRAT}$ delay based on the SRAT and to manage the pacing therapy delivered by the implantable device based in part on the $AV_{SRAT}$ delay.

2. The method of claim 1, wherein the septum activation time represents an onset of a Q-wave in a QRS complex.

3. The method of claim 1, wherein the sensing the CA signals includes sensing first CA signals over first sensing channel and sensing second CA signals over a second sensing channel simultaneously, the method further comprising:
    analyzing the first CA signals sensed over the first sensing channel to identify the RV activation; and
    analyzing the second CA signals sensed over the second sensing channel to identify a time of initial septum activation as the septum activation time, the septum activation time corresponding to a point in time at which the second CA signals sensed over the second sensing channel begin to rise above a baseline/neutral voltage level.

4. The method of claim 1, wherein the $AV_{SRAT}$ delay is based on an adjustment of a prior AV delay by an amount proportional to the SRAT.

5. The method of claim 4, wherein the $AV_{SRAT}$ delay is set equal to the prior AV delay minus a percentage of the SRAT.

6. The method of claim 1, wherein the measuring further comprises delivering a pacing pulse at one of the LV sites and detecting a related intrinsic event at the RV site, repeating the delivering and detecting operations in connection with the multiple LV sites.

7. The method of claim 1, wherein the identifying the RV activation time and the septum activation time further comprises:
    collecting the CA signals over first and second sensing vectors;
    analyzing the CA signals collected over the first sensing vector to identify the RV activation time corresponding to a feature of interest in an R-wave of a QRS complex;
    analyzing the CA signals collected over the second sensing vector to identify the septum activation time corresponding to a feature of interest in a Q-wave of the QRS complex.

8. The method of claim 1, further comprising determining an order of activation for the multiple LV sites based on the activation times.

9. A system for managing a pacing therapy using an implantable medical device (IMD), the system comprising:
    electrodes coupled to the IMD, the electrodes configured to be located proximate to multiple left ventricular (LV) sites and a right ventricular (RV) site of the heart, the electrodes configured to sense cardiac activity (CA) signals;
    memory to store program instructions; and
    one or more processors configured to implement the program instructions to:
        measure activation times between the multiple LV sites and the RV site based on the CA signals;
        identify an RV activation time and a septum activation time based on the CA signals;
        calculate a septum to RV activation time (SRAT) based on the RV and septum activation times; and
        set an $AV_{SRAT}$ delay based on the SRAT.

10. The system of claim 9, wherein the septum activation time represents an onset of a Q-wave in a QRS complex.

11. The system of claim 9, further comprising first and second sensing channels configured to sense first and second CA signals, respectively, simultaneously, the one or more processors further configured to:
    analyze the first CA signals sensed over the first sensing channel to identify the RV activation; and
    analyzing the second CA signals sensed over the second sensing channel to identify a time of initial septum activation as the septum activation time, the septum activation time corresponding to a point in time at which the second CA signals sensed over the second sensing channel begin to rise above a baseline/neutral voltage level.

12. The system of claim 9, wherein the $AV_{SRAT}$ delay is based on an adjustment of a prior AV delay by an amount proportional to the SRAT.

13. The system of claim 12, wherein the AVSRAT delay is set equal to the prior AV delay minus a percentage of the SRAT.

14. The system of claim 9, wherein the one or more processors are configured to perform the measure operation by delivering a pacing pulse at one of the LV sites and detecting a related intrinsic event at the RV site, repeating the delivering and detecting operations in connection with the multiple LV sites.

15. The system of claim 9, wherein the one or more processors are configured to identify the RV activation time and the septum activation time by:
    collecting the CA signals over first and second sensing vectors;
    analyzing the CA signals collected over the first sensing vector to identify the RV activation time corresponding to a feature of interest in an R-wave of a QRS complex; and
    analyzing the CA signals collected over the second sensing vector to identify the septum activation time corresponding to a feature of interest in a Q-wave of the QRS complex.

16. The system of claim 15, wherein the SRAT corresponds to a duration of the interval between the feature of interest in the R-wave and the feature of interest in the Q wave of the QRS complex.

17. The system of claim 9, wherein the one or more processors are configured to determine an order of activation for the multiple LV sites based on the activation times.

18. The system of claim 17, further comprising a lead that includes the electrodes, the lead coupled to the implantable medical device.

19. The system of claim 17, wherein the implantable medical device is a leadless device with the electrodes provided on the housing.

20. The system of claim 9, further comprising an external device (ED) configured to wirelessly communicate with the implantable medical device, the implantable medical device configured to transmit the CA signals to the external device;
  wherein the one or more processors include at least one IMD processor in the IMD and at least one ED processor in the ED, the at least one ED processor configured to perform the identify and calculate operations,
  the ED configured to wirelessly transmit the $AV_{SRAT}$ delay to the implantable medical device, the implantable medical device configured to utilize the $AV_{SRAT}$ delay in connection with delivering therapy.

* * * * *